United States Patent [19]

Bundy et al.

[11] 4,130,721

[45] Dec. 19, 1978

[54] 11-DEOXY PGE$_2$ COMPOUNDS

[75] Inventors: Gordon L. Bundy, Portage; Norman A. Nelson, Galesburg, both of Mich.

[73] Assignee: The Upjohn Company, Kalamazoo, Mich.

[21] Appl. No.: 274,650

[22] Filed: Jul. 24, 1972

[51] Int. Cl.$^2$ ............................................. C07C 177/00
[52] U.S. Cl. .............................. 560/121; 260/343.3 P; 260/410; 260/410.4 R; 260/346.22; 260/410.5; 260/413; 562/503; 424/305; 424/317; 542/426; 560/231

[58] Field of Search ............... 260/468 D, 514 D, 488

[56] References Cited

U.S. PATENT DOCUMENTS

| 3,691,216 | 9/1972 | Bergstrom | 260/468 |
|---|---|---|---|
| 3,736,319 | 5/1973 | Martel et al. | 260/240 |
| 3,801,623 | 4/1974 | Martel et al. | 260/468 |

FOREIGN PATENT DOCUMENTS 2121429 11/1971 Fed. Rep. of Germany ........... 260/468

OTHER PUBLICATIONS

Martel et al., Tetrahedron Letters, 1491 (1972).
Crabbe et al., Tetrahedron Letters, 115 (1972).

*Primary Examiner*—Robert Gerstl
*Attorney, Agent, or Firm*—Morris L. Nielsen

[57] ABSTRACT

11-Deoxyprostaglandin E and F type compounds, i.e. prostaglandin E and F type compounds in which the 11-hydroxy group is replaced by hydrogen, are disclosed, with processes for making them. These compounds are useful for a variety of pharmacological purposes, including anti-ulcer, inhibition of platelet aggregation, increase of nasal patency, labor inducement at term, and wound healing.

3 Claims, No Drawings

11-DEOXY PGE₂ COMPOUNDS

BACKGROUND OF THE INVENTION

This invention relates to novel compositions of matter, to novel methods for producing those, and to novel chemical intermediates useful in those processes. Particularly, this invention relates to certain novel analogs of prostaglandins $E_2$, $E_3$, $F_{2\alpha}$, $F_{2\beta}$, $F_{3\alpha}$, and $F_{3\beta}$ in which the 11-hydroxy is replaced by hydrogen, i.e. the ring carbon atom adjacent to the site of attachment of the methyl-terminated chain bears no hydroxyl substituent.

The known prostaglandins include, for example, prostaglandin $E_2$ ($PGE_2$), prostaglandin $F_2$ alpha and beta ($PGF_{2\alpha}$ and $PGF_{2\beta}$), prostaglandin $A_2$ ($PGA_2$), and the corresponding $PG_3$ compounds. Each of the above-mentioned known prostaglandins is a derivative of prostanoic acid which has the following structure and atom numbering:

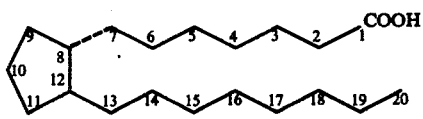

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

$PGE_2$ has the following structure:

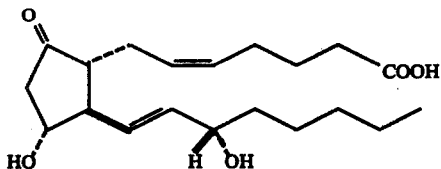

$PGF_{2\alpha}$ has the following structure:

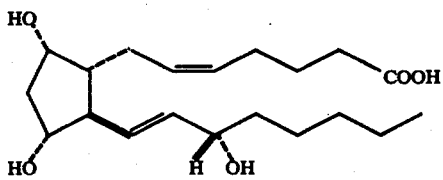

$PGF_{2\beta}$ has the following structure:

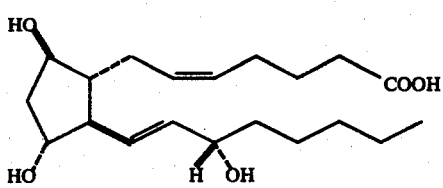

$PGA_2$ has the following structure:

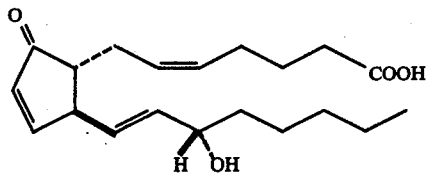

Each of the known $PG_3$ prostaglandins, $PGE_3$, $PGF_{3\alpha}$, $PGF_{3\beta}$, and $PGA_3$ has a structure the same as that shown for the corresponding $PG_2$ compound except that, in each, there is a cis carbon-carbon double bond between C-17 and C-18. For example, $PGE_3$ has the following structure:

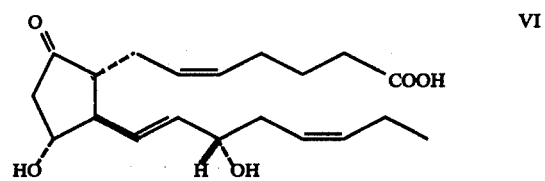

In formulas II to VI, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to VI is in S configurtion. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II to VI each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VI represents the other enantiomer of that prostaglandin. The racemic form of a prostaglandin contains equal numbers of both enantiomeric molecules, and one of formulas II to VI and the mirror image of that formula is needed to represent correctly the corresponding racemic prostaglandin. For convenience hereinafter, use of the terms $PGE_2$, $PGE_3$, $PGF_{2\alpha}$, and the like, will mean the optically active form of that prostaglandin with the same absolute configurtion as $PGE_1$ obtained from mammalian tissues When reference to the racemic form of one of those prostaglandins is intended, the word "racemic" or "dl" will preceed the prostaglandin name, thus, racemic $PGE_2$ or dl-$PGF_{2\alpha}$.

$PGE_2$, $PGE_3$, and the corresponding $PGF_\alpha$, $PGF_\beta$, and PGA compounds, and their esters, acylates, and pharmacologically acceptable salts, are extremely potent in causing various biological responses. For that reason, these compounds are useful for pharmacological purposes. See, for example, Bergstrom et al., cited above. A few of those biological responses are systemic arterial blood pressure lowering in the case of the PGE, $PGF_\beta$, and PGA compounds as measured, for example, in anesthetized (pentobarbital sodium) pentolinium-treated rats with indwelling aortic and right heart cannulas; pressor activity, similarly measured, for the $PGF_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 µg. to about 10 mg. per ml. of a pharmacologically suitable liquid vehicle or as an aerosol spray, both for topical application.

The PGE, $PGF_\alpha$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used one to four times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc); xanthine derivatives (theophylline and aminophyllin); and corticosteroids (ACTH and prednisolone). Regarding use of these compounds see South African Pat. No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arterioclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of steriile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF_\alpha$, and $PGF_\beta$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniquesfor organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in explusion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, PGF$_\beta$, and PGA compounds are useful as hypotensive agents to reduce blood pressure in mammals, including man. For this purpose, the compounds are administered by intravenous infusion at the rate of about 0.01 to about 50 μg. per kg. of body weight per minute, or in single or multiple doses of about 25 to 500 μg. per kg. of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephric states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intraveneous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE, PGF$_\alpha$, and PGF$_\alpha$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGF$_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusion of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Especially for topical use, these prostaglandins are useful in combination with antibiotics, for example, gentamycin, neomycin, polymyxin B, bacitracin, spectinomycin, and oxytetracyline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

SUMMARY OF THE INVENTION

It is a purpose of this invention to provide novel 11-deoxy prostaglandin E and F analogs in which there is variable chain length in the side chains. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The presently described acids and esters of the 11-deoxy prostaglandin E and F analogs include compounds of the following formulas, and also the racemic compounds of each respective formula and the mirror image thereof:

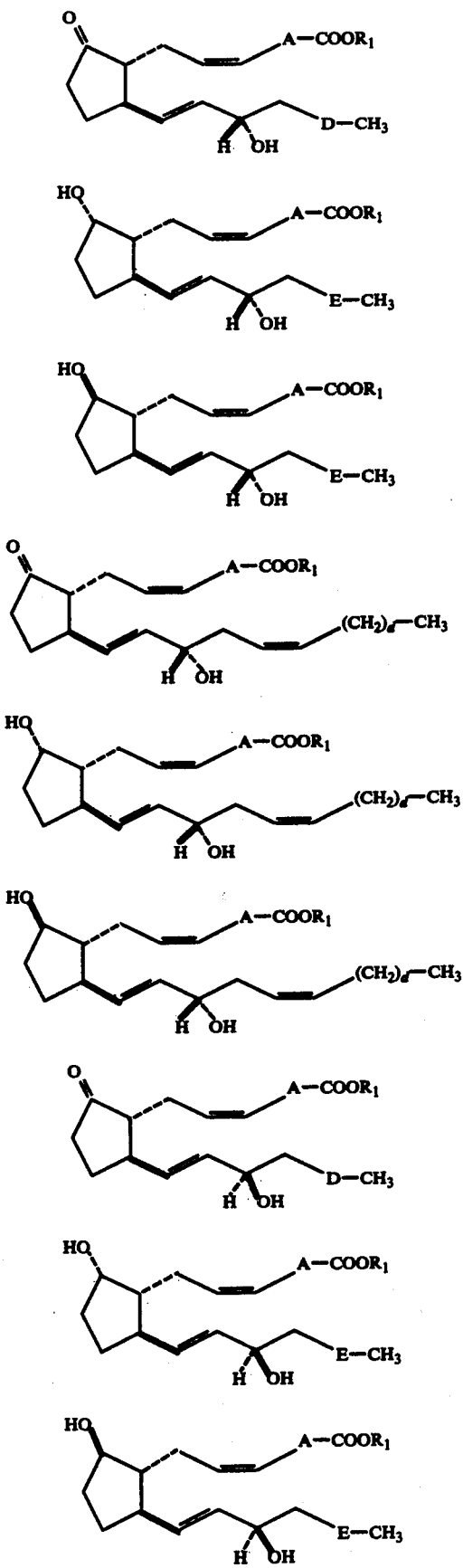

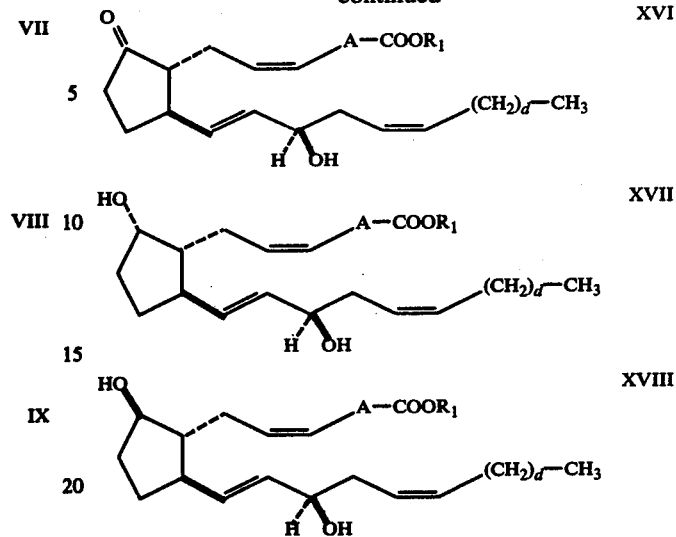

There are also included the alkanoates of 2 to 8 carbon atoms, inclusive.

In formulas VII to XVIII, inclusive, A is alkylene of one to 10 carbon atoms, inclusive, with one to five carbon atoms, inclusive, in the chain between —COOR$_1$ and

D is either a valence bond or alkylene of one to nine carbon atoms, inclusive, with one to five carbon atoms, inclusive, in the chain between —CH$_2$— and terminal methyl; E is (a) a valence bond, (b) alkylene of one or two carbon atoms, (c) branched-chain alkylene of three carbon atoms, or (d) alkylene of four to nine carbon atoms, inclusive, with one to five carbon atoms, inclusive, in the chain between —CH$_2$— and terminal methyl; d is 0, 1, 2, or 3; and R$_1$ is hydrogen, alkyl of one to 12 carbon atoms, inclusive, cycloalkyl of three to 10 carbon atoms, inclusive, aralkyl of seven to 12 carbon atoms, inclusive, phenyl, or phenyl substituted with one, two, or three chloro or alkyl of 1 to 4 carbon atoms, inclusive.

Formulas VII to XII represent 11-deoxyprostaglandin E and F type compounds, i.e. analogs of prostaglandins E$_2$, F$_{2\alpha}$, F$_{2\beta}$, E$_3$, F$_{3\alpha}$, and F$_{3\beta}$ in which the 11-hydroxy is replaced by hydrogen. For example, formula VII represents 11-deoxy-PGE$_2$ when A is —(CH$_2$)$_3$—, D is —(CH$_2$)$_3$—, and R$_1$ is hydrogen. Formula VIII represents 11-deoxy-20-methyl-2-nor-PGF$_{2\alpha}$ when A is —(CH$_2$)$_2$—, E is —(CH$_2$)$_4$—, and R$_1$ is hydrogen. Formula X represents 11-deoxy-2a-homo-PGE$_3$ when A is —(CH$_2$)$_4$—, d is 1, and R$_1$ is hydrogen. Formula XII represents 11-deoxy-PGF$_{3\beta}$, methyl ester, when A is —(CH$_2$)$_3$—, d is 1, and R$_1$ is methyl.

Formulas XIII to XVIII, inclusive, represents the corresponding 15-epi compounds, alternately named 15R compounds. For example, formula XIII represents 11-deoxy-15-epi-PGE$_2$, methyl ester, when A is —(CH$_2$)$_3$—, D is —(CH$_2$)$_3$—, and R$_1$ is methyl.

An alternate name for 11-deoxy PGE$_2$ is 10,11-dihydro PGA$_2$. These compounds may also be named as prostanoic acid derivatives. For example, 11-deoxy PGF₂ is (15S)-9α,15-dihydroxyprosta-cis-5,trans-13-dienoic acid.

In the name of the formula-VIII example above, "2-nor" indicates absence of one carbon atom from the carboxy-terminated side chain of the PGF$_{2\alpha}$ structure. Following the atom numbering of the prostanoic acid structure, C-2 is construed as missing. In this system of nomenclature, the words "nor", "dinor", "trinor", or "tetranor" in the names of the prostaglandin analogs are to be construed as indicating one, two, three, or four carbon atoms, respectively, missing from the C-2 to C-4 and the C-16 to C-20 positions of the prostacoic acid carbon skeleton. In addition, in the name of the formula-VIII example, "20-methyl" indicates that a methyl group replaces a hydrogen on C-20. The methyl-terminated chain of that example therefore has nine carbon atoms.

In the name of the formula-X example. "2a-homo" indicates one additional carbon atom in the carboxy-terminated side chain specifically between the C-2 and C-3 carbon atoms. There are, therefore, eight carbon atoms in that side chain instead of the normal seven in the prostanoic acid structure. From the end of the chain to the double bond of the example they are identified as C-1, C-2, C-2a, C-3, C-4, and C-5. The carbon atoms connected by the cis double bond are C-5 and C-6, and the carbon atoms between the double bond and the ring are C-6 and C-7.

As in the case of formulas II to VI, formulas VII, VIII, X, and XI are each intended to represent optically active prostanoic acid derivatives with the same absolute configuration as PGE₁ obtained from mammalian tissues. Formulas XIII to XVIII wherein M is

represent 15R (15-epi) compounds wherein the hydroxyl is attached to the side chain in beta configuration.

Also included within this invention are the 9-epimer compounds of formulas IX and XII wherein the C-9 hydroxy is in beta configuration. Hereinafter "PGF$_\beta$" refers to the epimeric configuration. Thus, the name of the formula-XII example above, "11-deoxy-PGF$_{2\beta}$, methyl ester, identified a compound having the beta configuration at C-9 instead of the natural alpha configuration.

Each of the formulas VII to XII plus its mirror image describe a racemic compound within the scope of this invention. For convenience hereinafger, such a racemic compound is designated by the prefix "racemic" ("rac" or "dl") before its name; when that prefix is absent, the intent is to designate an optically active compound represented by the appropriate formula VII to XII.

With regard to formulas VII to XII, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of three to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of seven to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to three chloro or alkyl of one to four carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkylene are methylene, ethylene, trimethylene, tetramethylene, and pentamethylene, and those alkylene with one or more alkyl substituents on one or more carbon atoms thereof, e.g., —CH(CH₃)—, —C(CH₃)₂—, —CH(CH₂CH₃)—, —CH₂—CH(CH₃)—, —CH(CH₃)—CH(CH₃)—, —CH₂—C(CH₃)₂—, —CH₂—CH(CH₃)—CH₂—, —CH₂—, CH₂—CH₂—CH(CH₂CH₂CH₃)—, and the like.

Accordingly, there is provided an optically active compound of the formula

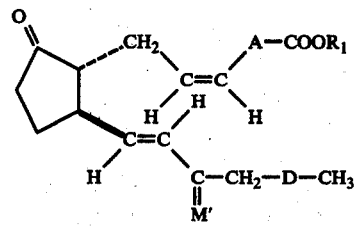

VII or a racemic compound of that formula and the mirror image thereof, wherein A is alkylene of one to 10 carbon atoms, inclusive, with one to five carbon atoms, inclusive, between

wherein D is either a valence bond or alkylene of one to nine carbon atoms, inclusive, with one to five carbon atoms, inclusive, in the chain between —CH₂— and terminal methyl; wherein M' is

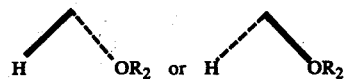

wherein R₂ is hydrogen or alkanoyl of two to eight carbon atoms, inclusive; and wherein R₁ is hydrogen, alkyl of one to 12 carbon atoms, inclusive, cycloalkyl of three to 10 carbon atoms, inclusive, aralkyl of seven to 12 carbon atoms, inclusive, phenyl, or phenyl substituted with one, two, or three chloro or alkyl of one to four carbon atoms, inclusive.

There is also provided an optically active compound of the formula

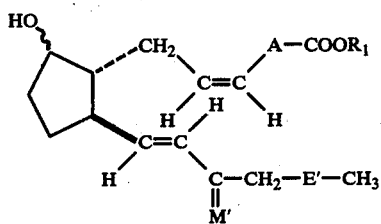

or a racemic compound of that formula and the mirror image thereof, wherein A is alkylene of one to 10 carbon atoms, inclusive, with one to five carbon atoms, inclusive, between —COOR$_1$ and

wherein E' is either a valence bond or alkylene of one or two carbon atoms; wherein M' is

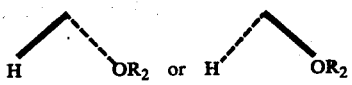

wherein R$_2$ is hydrogen or alkanoyl of two to eight carbon atoms, inclusive; wherein R$_1$ is hydrogen, alkyl of one to 12 carbon atoms, inclusive, cycloalkyl of three to 10 carbon atoms, inclusive, aralkyl of seven to 12 carbon atoms, inclusive, phenyl, or phenyl substituted with one, two or three chloro or alkyl of one to four carbon atoms, inclusive, and wherein ~ indicates attachment of hydroxyl to the ring in alpha or beta configuration.

Formula XIX represents 11-deoxy-PGF$_{2\alpha}$ analogs when ~ is alpha, and 11-deoxy-PGF$_{2\beta}$ analogs when ~ is beta.

There is further provided an optically active compound of the formula

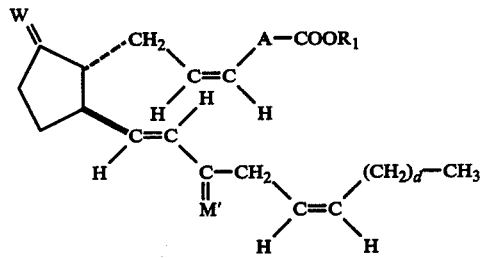

or a racemic compound of that formula and the mirror image thereof, wherein A is alkylene of one to 10 carbon atoms, inclusive, with one to five carbon atoms, inclusive, between —COOR$_1$ and

wherein M' is

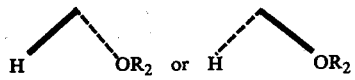

wherein R$_2$ is hydrogen or alkanoyl of two to eight carbon atoms, inclusive; wherein R$_1$ is hydrogen, alkyl of one to 12 carbon atoms, inclusive, cycloalkyl of three to 10 carbon atoms, inclusive, aralkyl of seven to 12 carbon atoms, inclusive, phenyl, or phenyl substituted with one, two, or three chloro or alkyl of one to four carbon atoms, inclusive; wherein W is O=,

or

and wherein d is 0, 1, 2, or 3.

Formula XX represents 11-deoxy-PGE$_3$ analogs when W is O=; 11-deoxy-PGF$_{3\alpha}$ analogs when W is

and 11-deoxy-PGF$_{3\beta}$ analogs when W is

The novel formula VII-to-XX compounds and the racemic compounds of this invention each cause the biological responses described above for the PGE, PGF$_\alpha$, PGF$_\beta$, and PGA compounds, respectively, and each of these novel compounds is accordingly useful for the above-described corresponding purposes, and is used for those purposes in the same manner as described above.

The known PGE, PGF$_\alpha$, PGF$_\beta$, PGA, and PGB compounds are all potent in causing multiple biological responses even at low doses. For example, PGE$_1$ and PGE$_2$ both cause vaso-depression and smooth muscle stimulation at the same time they exert antilipolytic activity. Moreover, for many applications, these known prostaglandins have an inconveniently short duration of biological activity. In striking contrast, the novel prostaglandin analogs of formulas VII to XX and their racemic compounds are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a differnt and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Because of their unique chemical structure, the novel prostaglandin analogs of this invention are less sensitive to rearrangement than the prostaglandins and enjoy increased chemical stability and longer shelf life.

To obtain the optimum combination of biological response specificity, potency, and duration of activity, certain compounds within the scope of formulas VII to XX are preferred. For example, it is preferred that the hydroxyl at C-15 be in the alpha configuration. It is also preferred that any branching of the $C_nH_{2n}$ group in the methyl-terminated chain be at C-16 or C-17. In the general expressions —D—CH$_3$ or —E—CH$_3$ as used herein, examples of such branching are —CH(CH$_3$)—CH$_3$, —CH(CH$_3$)—C$_2$H$_5$, —CH$_2$—CH(CH$_3$)—CH$_3$, —C(CH$_3$)$_2$—CH$_2$—CH$_3$, —CH(CH$_3$)—CH(CH$_3$)—CH$_3$, —C(CH$_3$)$_2$—C(CH$_3$)$_2$—CH$_2$—CH$_3$, —CH(CH$_3$)—(CH$_2$)$_2$—CH$_3$, and —C(CH$_3$)$_2$—(CH$_2$)$_5$—CH$_3$. Especially preferred are those wherein the —D—CH$_3$ chain length is three to five carbon atoms.

Another preference is that A be trimethylene when D has zero, one, two, three, four, or five carbon atoms in the chain between —CH$_2$— and terminal methyl. Still another preference is that D have three carbon atoms in the chain between —(CH$_2$— and terminal methyl when A has one, two, four, or five carbon atoms in the chain between —COOR$_1$ and

Another advantage of the novel compounds of this invention, especially the preferred compounds defined hereinabove, compared with the known prostaglandins, is that these novel compounds are administered effectively orally, sublingually, intravaginally, bucally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 11-deoxy prostaglandin E and F analogs encompassed by formulas VII to XX including their alkanoates, are used for the purposes described above in the free acid form, in ester form, or in pharmacologically acceptable salt form. When the ester form is used, the ester is any of those within the above definition of R$_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these formula VII-to-XX compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds encompassed by formulas VII to XX are used for the purposes described above in free hydroxy form or also in the form wherein the hydroxy moieties are transformed to lower alkanoate moieties, e.g., -OH to -OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas VII to XX are administered in various ways for various purposes; e.g., intravenously, intramuscularly, subcutaneously, orally, intravaginally, rectally, bucally, sublingually, topically, and in the form of sterile implants for prolonged action. For intravenous injection or infusion, sterile aqueous isotonic solutions are preferred. For that purpose, it is preferred because of increased water solubility that R$_1$ in the formula VII-to-XX compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers, are used for oral sublingual administration. For rectal or vaginal administration, suppositories prepared as known in the art are used. For tissue implants, a sterile tablet or silicone rubber capsule or other object containing or impregnated with the substance is used.

A number of 11-deoxy prostaglandins are reported in the literature. Subsequent to our invention, P. Crabbé and A. Gutzmán, Tetrahedronn Lett. No. 2, 115, 1972, reported the synthesis of dl-11-deoxy-PGE$_2$. dl-11-Deoxy-PGF$_{2\alpha}$ is also described in the same publication. Belgian Pat. No. 766,521 issued to Roussel-Uclaf claims 15α-hydroxy-9-oxo-5-cis-13-trans-prostadienoic acid (11-deoxy-PGE$_2$), its methyl ester, and its sodium salt. That patent also claims compounds of the general formula

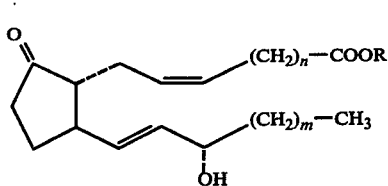

in which R represents hydrogen or lower alkyl, n is 2, 3, or 4, and m is 3, 4, or 5, including certain salts. J. Pike et al., Nobel Symposium 2, Prostaglandins, p. 161 (1967) report 11-deoxy-PGE$_1$, methyl ester, 11-deoxy-13,14-dihydro-PGE$_1$, methyl ester, 11-deoxy-13,14$\alpha$, and 11-deoxy-13,14-dihydro-PGF$_{1\beta}$. M. P. L. Caton et al., Tetrahedron Lett. No. 9, 773, 1972, report dl-11-deoxy-PGF$_1$ (see South African Pat. No. 71/0435). See also German Pat. No. 2,137,881 and U.S. Pat. Nos. 3,432,541, 3,455,992, and 3,524,867. See also O. Korver, Rec. Trav. Chim. 88, 1070 (1969), A. J. Weinheimer et al., Tetrahedron Lett. No. 59, 5185 (1969), R. Pappo et al., Ann. N.Y. Acad. Sci. 180, 64 (1971), R. Klok et al., Rec. Trav. Chim. 89, 1043 (1970), Beal et al., Novel Symposium 2, p. 219 (1967), and J. F. Bagli et al., Tetrahedron Lett. No. 5, 465 (1966).

The 11-deoxy prostaglandin E and F analogs encompassed by formulas VII through XX are produced by the reactions and procedures described and exemplified hereinafter.

Reference to Charts A and B herein will make clear the process steps, starting with a PGA$_2$ or PGA$_3$ type compound. In Chart A, the PGA compound of general formula XXI is reduced by alkali metal borohydride, thereby reducing ring unsaturation as well as reducing 9-oxo to 9-hydroxy. In Charts A and B, Z is either —CH$_2$CH$_2$— or cis —CH=CH—. The starting materials are readily available or are prepared by methods known in the art. See British Specification No. 1,097,533 issued Jan. 3, 1968. For example, PGA compounds are obtained from PGE compounds by acid dehydration. For racemic PGE compounds see Schneider, Chem. Commun. 304 (1969) and Axen et al., ibid 602 (1970).

The reduction to the formula-XXII compounds is accomplished with a reducing agent which reduces ring unsaturation and 9-oxo without reducing esters or olefinic unsaturation. For this purpose an alkali metal borohydride, e.g. sodium, potassium, or lithium borohydride is effective in aqueous solution. The reaction is carried out at about $-20°$ C. and is complete within a few minutes.

In the formula-XXI compound, M" is either

or

wherein R$_3$ is hydrogen, alkanoyl of two to eight carbon atoms, inclusive, tetrahydropyranyl, tetrahydrofuranyl, or a group of the formula

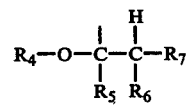

wherein R$_4$ is alkyl of one to 18 carbon atoms, inclusive, cycloalkyl of three to 10 carbon atoms, inclusive, aralkyl of seven to 12 carbon atoms, inclusive, phenyl, or phenyl substituted with one, two, or three alkyl of one to four carbon atoms, inclusive; wherein R$_5$ and R$_6$ are the same or different, being hydrogen, alkyl of one to 4 carbon atoms inclusive, phenyl, or phenyl substituted with one, two, or three alkyl of one to four carbon atoms, inclusive, or, when R$_5$ and R$_6$ are taken together, —(CH$_2$)$_a$— or —(CH$_2$)$_b$—O—(CH$_2$)$_c$— wherein a is 3, 4, or 5, b is 1, 2, or 3, and c is 1, 2, or 3 with the proviso that b plus c is 2, 3, or 4; and wherein R$_7$ is hydrogen or phenyl. If the desired product is a formula-XXIII 11-deoxy PGF are analog, R$_3$ is simply hydrogen. If, however, the formula-XXII intermediate is used to prepare a formula-XXVI 11-deoxy PGE analog, R$_3$ is preferably not hydrogen; if it is hydrogen it is replaced with a blocking group R$_8$ as will be discussed hereinafter. Likewise, R$_1$ is hydrogen, alkyl, cycloalkyl, aralkyl, phenyl, or substituted phenyl as defined above, the esters being readily obtained by methods known in the art.

CHART A

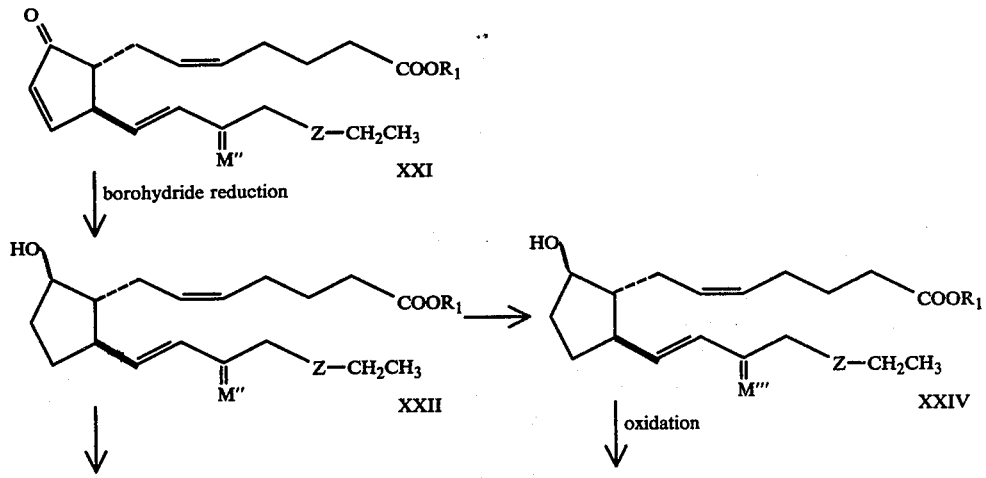

-continued
CHART A

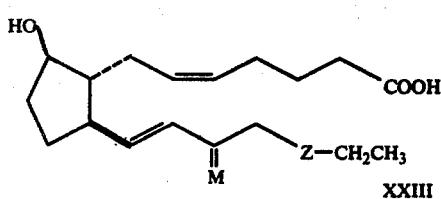
XXIII

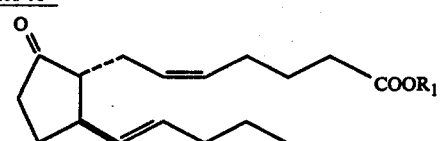
XXV

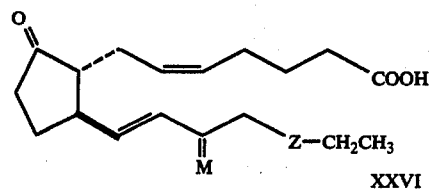
XXVI

CHART B

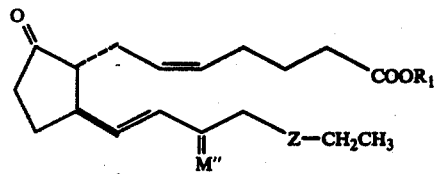
XXI hydrogen reduction

XXVII

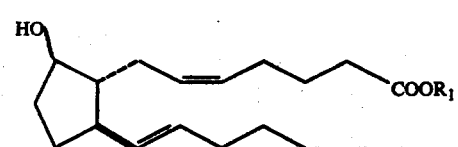
XXVI

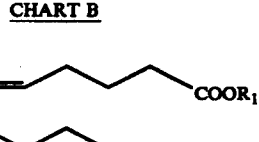
XXII

-continued
CHART B

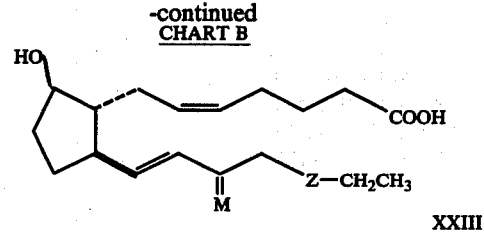
XXIII

To obtain the formula-XXIII 11-deoxy PGF analog, $R_1$ and $R_3$ of the formula-XXII intermediate are transformed to hydrogen by methods known in the art. Thus, $R_1$ is replaced by de-esterification, e.g. by alkaline hydrolysis at about 25° C. When $R_3$ is alkanoyl, e.g. acetyl, replacement with hydrogen is readily achieved by contacting the formula-XVI compound with an alkyli metal carbonate, for example, potassium carbonate, in methanol at about 25° C. When $R_3$ is tetrahydropyranyl or similar group including those derived from vinyl ethers, hydrolysis is achieved with methanol-HCl or with acetic acid/water/tetrahydrofuran at 40°-55° C.

Continuing with Chart A, the formula-XXII intermediate is transformed to a formula-XXVI 11-deoxy PGE analog by first replacing any hydrogen atoms of C-15 hydroxyls, i.e. where $R_3$ is hydrogen, with a blocking group $R_8$. In formula XXIV, M'''' is

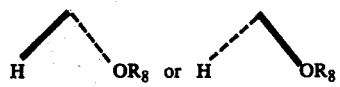

wherein $R_8$ is the blocking group. It is the function of this blocking group to prevent attack of the hydroxyl group by subsequent reagents, especially the oxidizing reagent for transforming

at C-9 to oxo. It is a further requirement of this blocking group that it be replaceable by hydrogen at a later stage in the preparation of the prostaglandin-like products. Blocking groups which have been found useful include alkanoyl, tetrahydropyranyl, tetrahydrofuranyl, a group of the formula

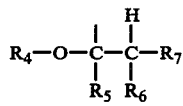

as defined above, and silyl of the formula —Si(G)₃ wherein G is alkyl of one to four carbon atoms, inclusive, phenyl, phenyl substituted with one or 2 fluoro, chloro, or alkyl of one to four carbon atoms, inclusive, or aralkyl of seven to 12 carbon atoms, inclusive.

In replacing the hydrogen of the hydroxyl group with an alkanoyl blocking group, methods known in the art are used. Thus, for example, acetic anhydride or acetyl chloride is reacted with the formula-XXII compound in the presence of a tertiary amine such as pyridine, triethylamine, and the like. The reaction is carried out under a variety of conditions using procedures generally known in the art. Generally, miled conditions are employed, e.g. 20°-60° C., contacting the reactants in a liquid medium, e.g. excess pyridine or an inert solvent such as benzene, toluene or chloroform. The acylating agent is used either in stoichiometric amount or in excess. If the acyl chloride is not available, it is made from the corresponding acid and phosphorus pentachloride or thionyl chloride as is known in the art.

When the blocking group is silyl of the formula —Si(G)₃, the formula-XXII compound is transformed to a silyl derivative of formula XXIV by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstitued monochlorosilanes suitable for this purpose include chlorotriethylsilane, chlorotriisobutylsilane, chlorotriphenylsilane, chlorotris(p-chlorophenyl)silane, chlorotri-m-tolylsilane, and tribenzylchlorosilane. Alternatively the chlorosilane is used with the corresponding disilazanes. Examples of other silylating agents suitable for forming the formula-XXIV intermediates include pentamethylsilylamine, pentaethylsilylamine, N-trimethylsilyldiethylamine, 1,1,1-triethyl-N,n-dimethylsilylamine N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilyamine, and 1-methyl-N,N,1,1-tetraphenylsilylamine.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in excess, preferably four to 10 times theory. The reaction is carried out at about 20°-50° C.

When the blocking group is of the formula

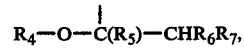

as defined above, the appropriate reagent is a vinyl ether, e.g. isobutyl vinyl ether or any vinyl ether of the formula R₄—O—C(R₅)=CR₆R₇ wherein R₄, R₅, R₆, and R₇ are as defined above; or an unsaturated cyclic or heterocyclic compound, e.g. 1-cyclohexen-1-yl methyl ether

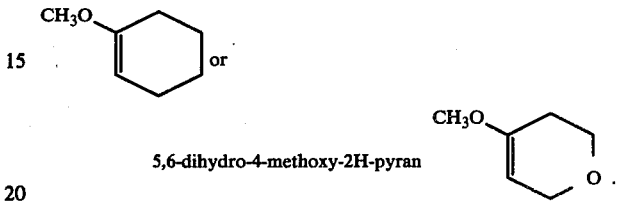

5,6-dihydro-4-methoxy-2H-pyran

See C. B. Reese et al., J. Am. Chem. Soc. 89, 3366 (1967). The reaction conditions for such vinyl ethers and unsaturates are similar to those for dihydropyran above.

The formula-XXIV intermediate is oxidized at C-9 to compound XXV. Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize one of the secondary hydroxy groups of the formula-XXIV reactant is used. Acetone is a suitable diluent for this purpose. Reaction temperatures at least as low as about 0° C. should be used. Preferred reaction temperatures are in the range −10° to −50° C. An especially useful reagent for this purpose is the Collins reagent, i.e. chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range −10° to +10° C. The oxidation proceeds rapidly and is usually complete in about 5 to 20 minutes. The formula-XXV PGE-type product is isolated by conventional methods.

Examples of other oxidation reagents useful for this transformation are silver carbonate on Celite (Chem. Commun. 1102 (1969)), mixtures of chromium trioxide and pyridine J. Am. Chem. Soc. 75, 422 (1953), and Tetrahedron, 18, 1351 (1962)), t-butylchromate in pyridine (Biochem. J., 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

To obtain the formula-XXVI product, the blocking groups on compound XXV are replaced with hydrogen, by hydrolysis as in preparing the PGF-type products of Chart A. Silyl groups are readily removed by prior art procedures known to be useful for transforming silyl ethers and silyl esters to alcohols and carboxylic acids, respectively. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necesary.

Likewise, $R_1$ of compound XXV is replaced with hydrogen, by methods known in the art. Thus, de-esterification is achieved by alkaline or enzymatic hydrolysis.

When the starting material has the "R" or epi configuration at C-15, i.e. M" is

the product is epimerized to the "S" or natural prostaglandin configuration by methods known in the art. See Bundy et al., J. Am. Chem. Soc. 94, 2123 (1972).

Referring next to Chart B, M, M", $R_1$, Z, and ~ have the same meaning as in Chart A. The formula-XXI starting material of Chart A is subjected to catalytic hydrogenation to reduce ring unsaturation without affecting olefinic chain unsaturation. For this purpose 5-10% palladium or rhodium catalysts on carbon, alumina, or other suitable supports are used. The reductions are carried out in any of a number of solvents, e.g. ethyl acetate, methanol, ethanol, or diethyl ether, at temperatures of $-30°$ to $+50°$ C. and pressures of about atmospheric to about 50 pounds per square inch.

The formula-XXVII intermediate is transformed to a formula-XXVI 11-deoxy PGE analog by replacing $R_1$ and $R_3$ with hydrogen as described above.

If a formula-XXIII 11-deoxy PGF analog is desired, the formula-XXVII intermediate is subjected to ring carbonyl reductions known in the art.

See, for example, Bergstrom et al., Arkiv Kemi 19, 563 (1963), Acta Chem. Scand. 16, 969 (1962), and British Specification No. 1,097,533. Any reducing agent is used which does not react with carbon-carbon double bonds or ester groups. Preferred reagents are lithium (tri-tertbutoxyl)aluminum hydride, the metal borohydrides, especially sodium, potassium, and zinc borohydrides, and the metal trialkoxy borohydrides, e.g., sodium trimethoxyborohydride or sodium triethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964).

Thereafter, the formula-XXII intermediate is transformed to PGF analogy XXIII by replacing $R_1$ and $R_3$ with hydrogen as described above.

In all of the above-described reactions, the products are separated by conventional means from the starting materials and impurities, for example by silica gel chromatography monitored by thin-layer chromatography (TLC).

Referring to Chart C, there is shown a general method for preparing 11-deoxy PGF analogs, starting with aldehyde XXVIII. See Corey et al., Tetrahedron Lett. No. 49, 4753 (1971) and Crabbé et al., ibid No. 2, 115 (1972). In Chart C, L is (a) a valence bond, (b) alkylene of one or two carbon atoms, (c) branched-chain alkylene of three carbon atoms (d) alkylene of four to nine carbon atoms, inclusive, with one to five carbon atoms, inclusive, in the chain between $-CH_2-$ and terminal methyl, or (e) cis$-CH=CH-(CH_2)_d-$ wherein d is 0, 1, 2, or 3; M is

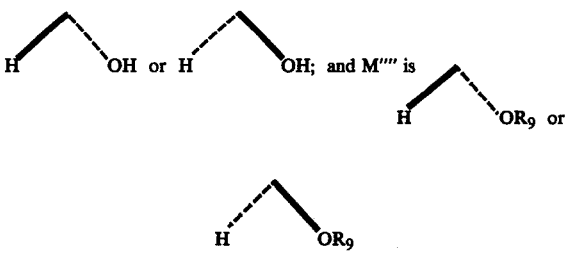

wherein $R_9$ is tetrahydropyranyl, tetrahydrofuranyl, or a group of the formula

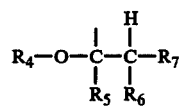

wherein $R_4$, $R_5$, $R_6$, and $R_7$ are as defined above.

CHART C

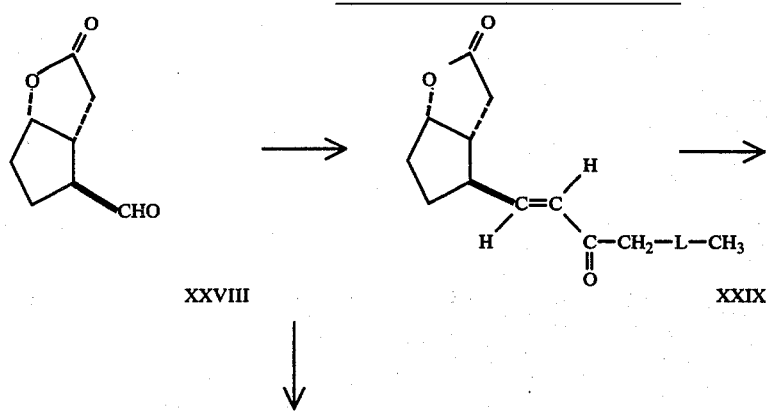

XXVIII  XXIX

CHART C -continued

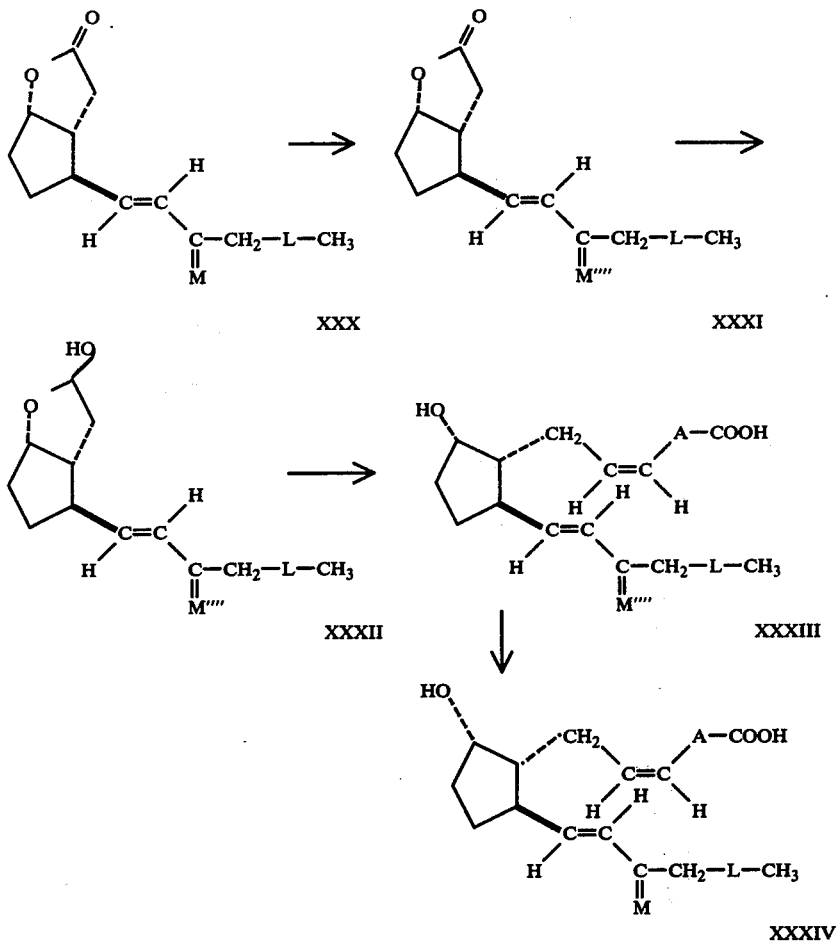

The formula-XXIX compound is obtained by Wittig alkylation of XXVIII, using the sodio derivative of the appropriate 2-oxo-alkyl (or alkenyl) phosphonate. The trans enone lactone is obtained stereospecifically. See D. H. Wadsworth et al., J. Org. Chem. 30. 680 (1965). For the Wittig reaction certain phosphonates are employed having the general formula

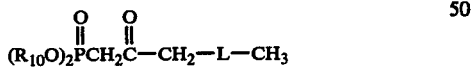

wherein $R_{10}$ is alkyl of one to eight carbon atoms, inclusive, and L has the same meaning as L of Charts C and D. The phosphonates are prepared and used by methods known in the art. See Wadsworth et al., Corey et al., and Crabbé et al., references cited above. Conveniently, the appropriate aliphatic acid ester is condensed purpose, dimethyl methylphosphonate in the presence of n-butyllithium. For this purpose acids of the general formula $CH_3-L-CH_2-COOH$ are used in the form of their lower alkyl esters, preferably methyl or ethyl. For example methyl esters are formed from the acids by reaction with diazomethane. These aliphatic acids of various chain length, with or without branching within the scope of L as defined above are known in the art or can be prepared by methods known in the art.

CHART D

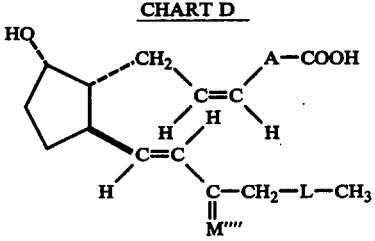 XXXIII

↓ oxidation

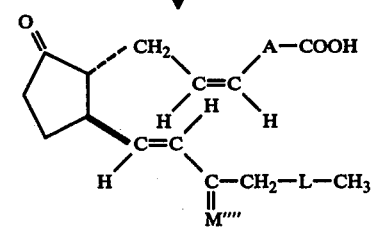 XXXV

↓ hydrolysis

-continued
CHART D

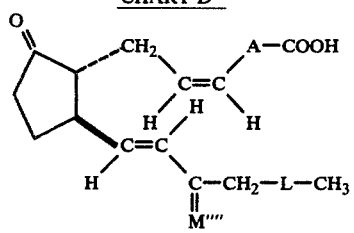

XXXVI the scope of L as defined above are known in the art or can be prepared by methods known in the art.

Aliphatic acids without branching are propionic, butyric, valeric, heptanoic, octanoic, nonanoic, decanoic, or undecanoic acids.

In the case of acids with branching, many are readily available, e.g. 2-methylpropionic, 2-methylbutyric, 2-ethylbutyric, 3-methylbutyric, 2,2-dimethylbutyric, 2-ethyl-2-methylbutyric, 2,2-diethylbutyric 2,3-dimethylbutyric, 3,3-dimethylbutyric, 2-methylvaleric, 2-propylvaleric, 3-methylvaleric, 2,2-dimethylvaleric, 3,3-diethylvaleric, 2-methyl-2-propylvaleric, 2-ethyl-3-methylvaleric, 2-methylhexanoic, 2-ethylhexanoic, 2-butylhexanoic, 2,2-dimethylhexanoic, 2,3-dimethylhexanoic, 2-butyl-2-methylhexanoic, 2-methylheptanoic, 2-propylheptanoic, 2-butylheptanoic, 2,2-diethylheptanoic, 2-methyl-2-propylheptanoic, 2-ethyloctanoic, 2-propyloctanoic, 3-methyloctanoic, 2-ethyl-2-methyloctanoic, 2-ethylnonanoic, 2,2-dimethylnonanoic, and 2-methyldecanoic acid. Other acids are available by methods known in the art, for example reaction of a branched alkyl halide with sodium cyanide to form a nitrile and subsequent hydroylsis to the acid.

Continuing with Chart C, the formula-XXX compound is obtained as a mixture of alpha and beta isomers by reduction of XXIX. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, and when carbon-carbon double bond reduction is not a problem, the boranes e.g., disiamylborane.

For production of natural-configuration PG-type compounds, the desired alpha (S) form of the formula-XXX compound is separated from the beta isomer by silica gel chromatography.

The formula-XXXI intermediate, wherein the hydrogen atoms of the M-hydroxyls are replaced with a blocking group $R_9$, is prepared by methods known in the art, for example using the conditions set forth above for dihydropyran, dihydrofuran, or substituted vinyl ethers. Especially preferred for $R_9$ are tetrahydropyranyl or (α-ethoxy)ethyl.

Alternatively, the formula-XXX compound is obtained from aldehyde XXVIII by a Wittig reaction employing a phosphonium salt, for example $(C_6H_5)_3P^+CH_2CH(OH)CH_2CH_3\ I^-$.

The lactol XXXII is obtained on reduction of the formula-XXXI lactone, using, for example, diisobutylaluminum hydride. The reduction is preferably done at $-60°$ to $-70°$ C.

The formula-XXXIII compound is obtained from the formula-XXXII lactol by the Wittig reaction, using a Wittig reagent derived from the appropriate ω-carboxyalkyltriphenylphosphonium bromide, HOOC—A—CH$_2$—P(C$_6$H$_5$)$_3$Br, and sodio dimethylsulfinylcarbanide. The reaction is conveniently carried out at about 25° C. This formula-XXXIII compound serves as an intermediate for preparing either the 11-deoxy PGF analog of Chart C or the 11-deoxy PGE analog of Chart D. The phosphonium compounds are known in the art or are readily available, e.g. by reaction of an ω-bromoaliphatic acid with triphenylphosphine.

The formula-XXXIV product is obtained by hydrolysis of the formula-XXXIII intermediate, thereby replacing $M''''$ with M, i.e. transforming $R_9$ to hydrogen.

Referring to Chart D, A, L, N, and $M''''$ have the same meaning as in Chart C. The 11-deoxy PGE analogs are obtained by oxidizing the formula-XXXIII intermediates and thereafter replacing $R_9$ with hydrogen. For the oxidation, either the Jones or Collins reagent is employed, following the conditions discussed above for Chart A. Finally, the blocking groups are removed by hydrolysis as discussed above to yield the formula-XXXVI products.

Optically active compounds are obtained from optically active intermediates according to the process steps of Charts A, B, C, and D. When racemic intermediates are used in reactions corresponding to the processes of Charts A-D, inclusive, and racemic products are obtained, these racemic products may be used in their racemic form or, if preferred, they may be resolved as optically active isomers by procedures known in the art.

For example, when final compound VII to XIV is a free acid, the dl form thereof is resolved into the d and l forms by reacting said free acid by known general procedures with an optically active base, e.g., brucine or strychnine, to give a mixture of two diastereiosimers which are separated by known general procedures, e.g., fractional crystallization, to give the separate diastereiosiomeric salts. The optically active acid of formula VII to XIV is then obtained by treatment of the salt with an acid by known general procedures.

Referring to Chart C, when a formula-XXX compound is prepared by reacting a racemic compound corresponding to formula XXVIII with a racemic Wittig reagent, there are obtained two pairs of racemates which are separable into pairs of racemic compounds by methods known in the art, e.g. silica gel chromatography. When a racemic compound corresponding to formula XXVIII is reacted with an optically active isomer of the Wittig reagent, there are obtained two diastereomers corresponding to the formula-XXX compound which are separated by conventional methods, e.g. by silica gel chromatography.

It is preferred that the formula-XXVIII compound be used in the optically active form which will lead to an 11-deoxy prostaglandin analog of the natural configuration. For this purpose, there is provided a process for resolving a racemic mixture of an oxo compound of the formula

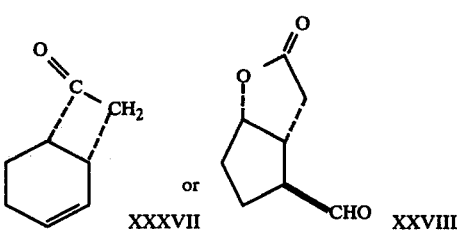

and of the mirror image thereof, which comprises the steps of (a) converting the oxo compound by reaction with an optically active ephedrine to a mixture of oxazolidine diastereomers, (b) separating at least one oxazolidine diastereomer from said mixture, (c) hydrolyzing said oxazolidine to free the optically active oxo compound, and (d) recovering said optically active oxo compound.

In carrying out the resolution of the formula-XXXVII ketone, there is prepared an oxazolidine by reaction of the ketone with an optically acitve ephedrine, e.g. d- or l-ephedrine, or d- or l-pseudoephedrine. Approximately equimolar quantities of the reactants are employed in a solvent such as benzene, isopropyl ether, or dichloromethane. The reaction proceeds smoothly over a wide range in temperature, for example 10° to 80° C., although for some reactants the range 20° to 30° C. is preferrred for convenience. The reaction occurs quickly, within minutes, whereupon the solvent is removed, preferably under vacuum. The product consists of the diastereomers of the ketone-ephedrine product, i.e. the oxazolidines. At least one of the diastereomers is separated by methods known in the art, including crystallization and chromatograhy. In this instance, crystallization is used as the preferred method. Repeated recrystallization of the thus-obtained solid oxazolidine from a suitable solvent, e.g., isopropyl ether, yields one of the diastereomers in substantially pure form. The oxazolidine is then hydrolyzed by procedures known in the art to release the ketone.

The mother liquor from th recrystallized diastereomer contains the optical isomer having opposite configuration. A preferred method for isolating this second diastereomer, however, is to prepare the oxazolidine of the racemic ketone using ephedrine of the opposite configuration to that first employed above, and thereafter recrystallizing as above. Finally, hydrolysis and recovery yield the resolved formula-XXXVII ketone in opposite configuration to that first obtained above.

Each optically active ketone can be converted to an aldehyde of the formula

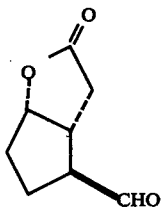 XXVIII or the mirror image thereof, using the procedures of Corey et all, Tetrahedron Lett. No. 49, 4753 (1971). That ketone is especially useful which yields the formula-XXVIII aldehyde which produces the 11-deoxy prostaglandin analogs having the natural configuration.

Likewise, the above process of resolution applied to the racemate containing the formula-XXVIII aldehyde yields the optically active formula-XXVIII aldehyde which produces the 11-deoxy prostaglandin analogs having the natural configuration.

As discussed above, the processes of Charts A-D, inclusive, lead variously to acids ($R_1$ is hydrogen) or to esters ($R_1$ is alkyl, cycloalkyl, aralkyl, phenyl or subsituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterifiction reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about 1 to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final formula VII-to-XX compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depnds in part upon the solubility characteristics of the particular salt to be prepared. In the case of the inorganic salts, it is usually suitable to dissolve the formula VII-to-XX acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lowe alknaol or a lower alkanone, gives the solid inorganic salt if that form is desired.

To produce an amine salt, the formula VII-to-XX acid is dissolved in a suitable solvent of either moderate or low polarity, Examples of the former are ethanol, acetone, and ethyl acetate. Examples of the latter are diethyl ether and bennzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VII-to-XX acid with the stoichiometric amount of the corresponding quaternary ammonium hydroxide in water solution, followed by evaporation of the water.

The final formula VII-to-XX acids or esters prepared by the processes of this invention are transformed to lower alkanoates by interaction of the formula VII-to-XX hydroxy compound with a carboxyacylating agent, preferably the anhydride of a lower alkanoic acid, i.e., an alkanoic acid of two to eight carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxylacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine ro neutralize the carboxylic acid produced by the reaction, as well as any free carboxyl groups present in the hydroxy compound reactant.

The carboxylacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 -hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula VII, X, XIII, and XVI 11-deoxy PGE-type compounds are transfored to monoalkanoates and the formula VIII, IX, XI, XII, XIV, XV, XVII, and XVIII 11-deoxy PGF-type compounds are transformed to dialkanoates.

When a PGE-type monoalkanoate is transformed to a PGF-type compound by carbonyl reduction as shown in Chart B, a PGF-type monoalkanoate is formed and is used for the above-described purposes as such or is transformed to a dialkanoate by the above-described procedure. In the latter case, the second alkanoyloxy group can be the same as or different from the alkanoyloxy group present before the carbonyl reduction.

DESCRIPTION OF THE PREFERRED EMBODIMENTS

The invention can be more fully understood by the following preparations and examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer in deuterochloroform solutions with tetramethylsilane as an internal standard (downfield).

"Brine", herein, refers to an aqueous saturated sodium chloride solution.

Preparation 1

Dimethyl 2-oxooctylphosphonate,

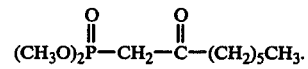

n-Butyllithiium (130 ml. of 1.6 M. solution) is slowly added to a solution of dimethyl methylphosphonate (25.6 g.) in 475 ml. of tetrahydrofuran (THF) at about $-65°$ C. To the mixture is added a solution of ethyl heptanoate (18.4 g.) in 50 ml. of THF, annd the resulting mixture is stirred at about $-70°$ C. for 2 hrs. Then, 16 ml. of acetic acid is added, and the mixture is concentrated under reduced pressure. The residue is mixed with dichloromethane (about 400 ml.) and water (about 50 ml.) shaken, and separated. The organic phase is dried over magnesium sulfate and concentrated. Distillation yields the title compound.

Preparation 2

3-Carboxypropyltriphenylphosphonium Bromide, $Br(C_6H_5)_3P(CH_2)_3COOH$.

Triphenylphosphine (156.8 g.) and 4-bromobutyric acid (100g.) are heated in 125 ml. of benzene at reflux for 18 hrs. The crystalline product is filtered off, washed with benzene, and recrystallized from ethwnol-acetonitrile-ether; 150 g., m.p. 247°–249° C.

Preparation 3

5-Carboxypentyltriphenylphosphonium bromide, $Br(C_6H_5)_3PC_5H_{10}COOH$.

Triphenylphosphine (156 g) and 6-bromohexanoic acid (115 g.) are heated in 125 ml. of benzene at reflux for 18 hrs. The crystalline product is filtered off, washed with benzene, and recrystallized from methanol-diethyl ether, m.p. 201°–203° C.

Example 1

11-Deoxy-PGE$_2$, Methyl Ester (Formula VII: A is —(CH$_2$)$_3$—, D is —(CH$_2$)$_3$—, and R$_1$ is methyl).

Refer to Charts A and B. A solution of sodium borohydride (7.0 g.) in 10 ml. of water and 90 ml. of cold ($-20°$ C.) methanol is added quickly to a cold solution of 15-epi-PGA$_2$, acetate, methyl ester (see A. J. Weinheimer et al., Tetrahedron Letters No. 59, pp. 5185–5188, 1969) (5.0 g.) in 100 ml. of methanol. The mixture is stirred at $-20°$ C. for 15 min. and 7 ml. of acetic acid is added cautiously, followed by 100 ml. of water. The mixture is concentrated under reduced pressure to an aqueous residue which is then extracted with dichloromethane. The organic phase is washed with dilute sodium bicarbonate solution and brine, dried and concentrated under reduced pressure to yield the mixed 9-alpha and 9-beta isomers of 11-deoxy-15-epi-PGF$_2$, 15-acetate, methyl ester, 5.0 g.

B. To a cold (−5° C.) solution of the product of step A above in 250 ml. of acetone is added dropwise with stirring over a 5-min. period 10 ml. of Jones reagent (21 g. chromium trioxide/60 ml. water/17 ml. conc. sulfuric acid). The mixture is stirred at 0° C. for 10 min., then 2 ml. of isopropanol is added and stirring continued for 5 min. The supernatant liquid is concentrated under reduced pressure. The residues are extracted with dichloromethane in the presence of cold dilute hydrochloric acid. The organic phase is washed with cold dilute hydrochloric acid, water, and brine, dried and concentrated. The residue is chromatographed on a silica gel column, eluting with 25% ethyl acetate-Skellysolve B (mixed isomeric hexanes). Those fractions shown by TLC (thin-layer chromatography) to contain 11-deoxy-15-epi-PGE$_2$, acetate, methyl ester (Formula XIII) are combined and concentrated to yield 3.0 g.; NMR peaks at 5.0–5.7, 3.6 (singlet), and 2.0 δ.

C. A mixture of 11-deoxy-15-epi-PGE$_2$, acetate, methyl ester (step B, 3.0 g.) in 50 ml. of methanol, and sodium hydroxide (1.5 g.) in 10 ml. of water is stirred at about 25° C. for several hours and then concentrated to an aqueous residue. The residue is shaken with ice, dichloromethane, and cold, dilute hydrochloric acid. The organic phase is washed with water and brine, dried, and concentrated to yield 11-deoxy-15-epi-PGE$_2$ (Formula XIII).

A solution of the above product in 25 ml. of diethyl ether is mixed with excess ethereal diazomethane. After 3 min. acetic acid is added and the solution is washed with cold dilute hydrochloric acid, dilute sodium bicarbonate solution, water, and brine, dried, and concentrated under reduced pressure to the formula-XIII 11-deoxy-15-epi-PGE$_2$, methyl ester; NMR peaks at 5.05–5.7, and 3.63 (singlet) δ.

D. Finally, the product of step C is epimerized to the title compound as follows. To a solution of 11-deoxy-15-epi-PGE$_2$ methyl ester (step C, 2.8 g.) in 50 ml. of pyridine at −15° C. is added 2.0 ml. of methanesulfonyl chloride. The mixture is stirred at −15° C. for 1.5 hrs. Then, 50 g. of ice is added, with stirring, and the mixture is shaken with diethyl ether-methylene chloride and 400 ml. of ice and water containing 50 ml. of conc. hydrochloric acid. The organic phase is washed with brine, dried, and concentrated under reduced pressure. The product is chromatographed on a silica gel column, eluting with 25–50% ethyl acetate in Skellysolve B. Those fractions shown by TLC to contain the product free of starting material and impurities are combined and concentrated to yield the title compound, 540 mg.; NMR peaks at 3.53–5.66 (multiplet), 5.28–5.43 (multiplet), and 3.63 (singlet) δ.

Example 2

11-Deoxy-PGE$_2$ (Formula VII: A is —(CH$_2$)$_3$—, D is —(CH$_2$)$_3$—, and R$_1$ is hydrogen).

Refer to Charts A and B. A. A solution of PGA$_2$, acetate, methyl ester (Br. Patent No. 1,097,533) (3.4 g.) in 68 ml. of methanol is cooled to −20° C. and mixed with a cold solution of sodium borohydride (4.7 g.) in 6.8 ml. of water and 61 ml. of methanol, added in portions. After additional stirring for 15 min., 4.7 ml. of acetic acid and 68 ml. of water are added. The mixture is concentrated under reduced pressure and extracted with dichloromethane. The aqueous phase is washed, dried, and concentrated to an oil which is the mixed 9-alpha and 9-beta isomers of 11-deoxy-PGF$_2$, 15-acetate, methyl ester, about 4 g.

B. A solution of the product of step A in 170 ml. of acetone is cooled to −5° C. and, while stirring, is treated dropwise with 6.8 ml. of Jones reagent (Example 1) over a 5-min. period. After additional stirring for 10 min., 1.4 ml. of isopropanol is added. The supernatant is concentrated and extracted with dichloromethane; the organic phase is washed, dried, and concentrated to an oily residue. The residue is chromatographed on silica gel, eluting with 20% ethyl acetate in Skellysolve B. Those fractions shown by TLC to contain the desired product free of starting material and impurities are combined and concentrated to yield 11-deoxy-PGE$_2$, acetate, methyl ester, 1.9 g.

C. The product of step B is treated with sodium hydroxide (0.9 g.) in 30 ml. of methanol and 6 ml. of water at about 25° C. for 1 hr. The mixture is acidified and concentrated, and then extracted with dichloromethane. The organic phase is concentrated to yield the title compound, 1.68 g. An analytical sample is obtained by chromatography over silica gel, eluting with 50% ethyl acetate-Skellysolve B, m.p. 42°–3° C.; infrared absorption peaks at 3360, 3300, 2710, 2650, 1725, 1325, 1300, 1275, 1185, 1020, and 980 cm$^{-1}$; and NMR peaks at 7.08, 5.6, 5.37, 4.1, and 0.9 δ.

Example 3

11-Deoxy-PGE$_2$ (Formula VII: A is —(CH$_2$)$_3$—, D is —(CH$_2$)$_3$, and R$_1$ is hydrogen).

Refer to Chart C. A solution of PGA$_2$ (4.0 g.) in 100 ml. of ethyl acetate is mixed with 400 mg. of a 5% palladium-charcoal catalyst and subjected to one atmosphere of hydrogen, first at −20° C., then at −10° C. and finally at −5° C. until no PGA$_2$ is evident by TLC. The mixture is filtered and concentrated. The oily residue is a mixture as shown by TLC and is subjected to silica gel chromatography, eluting with 20–50% ethyl acetate in Skellysolve B. Of six fractions, the fifth is found by TLC to contain the desired product mixed with 11-deoxy-PGE$_1$. Crystallization removes much of the 11-deoxy-PGE$_1$, and additional separation is achieved by chromatography on silica gel impregnated with silver nitrate. There is obtained the title compound, 58 mg., m.p. 41°–3° C., having the same NMR and infrared absorption spectra as the product of Example 2.

Example 4

11-Deoxy-PGF$_{2\alpha}$ (Formula VIII: A and E are —(CH$_2$)$_3$—, annd R$_1$ is hydrogen), and 11-Deoxy-PGF$_{2\beta}$ (Formula IX: A and E are —(CH$_2$)$_3$— and R$_1$ is hydrogen).

A. Following the procedure of Example 2A, a mixture of the 9-alpha and 9-beta isomers of 11-deoxy-PGF$_2$, 15-acetate, methyl ester is prepared. The mixture is chromatographed on silica gel, eluting with 50–75% ethyl acetate in Skellysolve B (mixed isomeric hexanes), combining and concentrating those fractions shown by TLC (thin layer chromatography) to contain the separated isomers free of impurities. There is thus obtained 11-deoxy-PGF$_{2\alpha}$, 15-acetate, methyl ester and 11-deoxy-PGF$_{2\beta}$, 15-acetate, methyl ester.

B. The 9-alpha product of Part A is treated with about 3% sodium hydroxide in aqueous methanol at about 25° C. for 1 hr. The mixture is acidified and concentrated, and then extracted with dichloromethane.

The organic phase is concentrated to yield the formula-VIII title compound.

C. Following the procedure of step B, the 9-beta isomeric product of part A is converted to the formula-IX title compound.

Example 5

Resolution of Bicyclo[4.2.0]oct-2-en-7-one.

A. A solution of the racemic formula-XXXVII ketone (E. J. Corey et al., Tetrahedron Lett. No. 49, 4753 (1971) 1.22 g.) and l-ephedrine (1.65 g.) in 15 ml. of benzene, together with a drop of acetic acid, is heated at reflux for about 5.5 hrs., using a Dean and Stark trap to remove water. The benzene is then removed by evaporation leaving the formed oxazolidines as solids which are dissolved in methanol. On cooling the methanol solution, there is obtained crystals of one of the diastereomeric oxazolidines.

The oxazolidine is hydrolyzed to the oxo compound and ephedrine by contact with water, preferably with an acid catalyst, as is known in the art (see Elderfeld Heterocyclic Compounds, Vol. 5 page 394, Wiley, N.Y. 1957). Thus, the above oxazolidine (1.3 g.) is stirred in a solution of tetrahydrofuran-water-acetic acid (25 ml.:25 ml.:5 ml.) for 4 hrs. at about 25° C. under nitrogen. The solvents are removed under reduced pressure and the residue is mixed with 25 ml. of water. The mixture is extracted several times with benzene, and the combined benzene layers are washed with water, dried over sodium sulfate, and concentrated under reduced pressure to yield an optically active isomer of the title compounds; called "the isomer of Example 5-A" herein.

B. The methanolic mother liquor from A is concentrated and chilled to yield another diastereomeric oxazolidine. Following the procedure of step A, the second oxazolidine is hydrolyzed to yield the corresponding enantiomer of the title compound; called "the isomer of Example 5-B" herein.

Example 6

Resolution of 3,3a$\beta$,4$\alpha$,5,6,6a$\beta$-Hexahydro-2oxo-2H-cyclopenta[b]furan-4-carboxaldehyde.

A. A solution of the racemic formula-XXVIII title compound (E. J. Corey et al., Tetrahedron Lett. No. 49, 4753 (1971) 15.4 g.) and l-ephedrine (16.5 g.) in 150 ml. of benzene is concentrated under reduced pressure to a residue. The residue is triturated with diethyl ether and then dissolved in isopropyl ether. The solution is chilled to yield crystals of one of the diastereomeric oxazolidines.

Hydrolysis of the oxazolidine, following the procedure of Example 5 yields an optically active isomer of the title compound; called "the isomer of Example 6-A" herein.

B. Following the procedure of Example 6-A above, but replacing l-ephedrine with d-ephedrine, there is obtained another diastereomeric oxazolidine which yields on hydrolysis an enantiomer of the isomer of Part A; called "the isomer of Example 6-B" herein.

Example 7

11-Deoxy-20-methyl-2-nor-PGF$_{2\alpha}$(Formula VIII: A is —(CH$_2$)$_2$—, E is —(CH$_2$)$_4$—, and R$_1$ is hydrogen).

Refer to Chart C. A. There is first prepared 5$\alpha$-hydroxy-2$\beta$-(3-oxo-trans-1-nonenyl)-1$\alpha$-cyclopentaneacetic acid $\gamma$-lactone (formula XXIX wherein L is —(CH$_2$)$_4$—). A solution of the formula-XXVIII 3,3a$\beta$,4$\alpha$,5,6,6a$\beta$-hexahydro-2-oxo-2H-cyclopenta[b]furan-4-carboxaldehyde (isomer of negative rotation of Example 6,3.0 g.) in 30 ml. of dichloromethane is added to a solution of the anion of dimethyl 2-oxooctylphosphonate prepared from that compound (Preparation 1, 6.6 g.) and sodium hydride (1.35 g.) in 50 ml. of tetrahydrofuran. The resulting reaction mixture is stirred for 2 hrs. at about 25° C., then acidified with acetic acid and concentrated under reduced pressure. The residue is partitioned between dichloromethane and water, and the organic phase is concentrated. The residue is chromatographed on silica gel, eluting with ethyl acetate-Skellysolve B (isomeric hexanes) (1:1). Those fractions shown by TLC to be free of starting material and impurities are combined and concentrated to yield the desired lactone.

B. The formula-XXX compound, 5$\alpha$-hydroxy-2$\beta$-(3$\alpha$-hydroxy-trans-1-nonenyl)-1$\alpha$-cyclopentaneacetic acid $\gamma$-lactone, is next prepared. A solution of the product of Part A above (4.65 g.) in 30 ml. of 1,2-dimethoxyethane is added to a mixture of zinc borohydride prepared from zinc chloride (anhydrous, 7.95 g.) and sodium borohydride (1.75 g.) in 71 ml. of dry 1,2-dimethoxyethane, with stirring and cooling to −10° C. Stirring is continued for 2 hrs. at 0° C., and water (12 ml.) is cautiously added, followed by 25 ml. of ethyl acetate. The mixture is filtered, and the filtrate is separated. The ethyl acetate solution is washed with brine, dried over sodium sulfate, and concentrated under reduced pressure to a mixture of the formula-XXX isomers. The alpha and beta hydroxy isomers are separated by chromatography on a silica gel column, eluting with ethyl acetate. The fractions containing the respective compounds are concentrated to yield the desired hydroxy intermediates.

C. The formula-XXXI tetrahydropyranyl ether is prepared by stirring a solution of the alpha hydroxy product of Part B (1.4 g.), 4.3 ml. of dihydropyran, and p-toluenesulfonic acid (0.023 g.) in 30 ml. of dichloromethane at about 25° C. for 30 min. The solution is washed with potassium bicarbonate solution, dried, and concentrated under reduced pressure.

D. The formula-XXXII lactol, namely 5$\alpha$-hydroxy-2$\beta$-(3$\alpha$-hydroxy-trans-1-nonenyl)-1$\alpha$-cyclopentaneacetaldehyde $\gamma$-lactol, tetrahydropyranyl ether, is next prepared. Diisobutylaluminum hydride (2.5 ml.) in 16 ml. of toluene is added dropwise to a stirred solution of the formula-XXXI tetrahydropyranyl ether (part C above, 3.0 g.) in 25 ml. of toluene cooled to −70° C. Stirring is continued at −70° C. for 30 min., whereupon a solution of 9 ml. of THF and 4.6 ml. of water is cautiously added. The mixture is filtered and the filtrate is washed with brine, dried, and concentrated to the mixed alpha and beta hydroxy isomers of the formula-XXXII compound.

E. The formula-XXXIII 15-tetrahydropyranyl ether of the title compound is prepared as follows. 3-Carboxypropyl triphenylphosphonium bromide (Preparation 1, 10.5 g.) is added to a solution of sodio dimethylsulfinylcarbanide prepared from sodium hydride (57%, 2.0 g.) and 50 ml. of DMSO, and the mixture is stirred for 20 min. at about 25° C. To this reagent is added dropwise the formula-XXXII lactol (Part D above, 2.8 g.) in 9 ml. of DMSO. The mixture stirred at about 25° C. for 2 hrs., then diluted with about 30 ml. of benzene. To it is added dropwise a solution of potassium hydrogen sulfate (6.4 g.) in 30 ml. of water, with cooling and stirring. The organic layer is separated, washed with water, dried, and concentrated under reduced pressure. The residue is chromatographed over silica gel using chloroform-methanol (10:1) for elution, to yield the formula-XXXIII compound.

F. The title compound is obtained by hydrolyzing the formula-XXXIII tetrahydropyranyl ether (Part E above, 0.8 g.) in a mixture of 5.6 ml. of THF and 18.6 ml. of 67% (aqueous) acetic acid. The mixture is warmed to about 40°–50° C. for 2 hrs., then concentrated under 1 mm. pressure. The residue is dissolved in benzene and chromatographed over silica gel using chloroform-methanol (4:1) for elution. Those fractions shown by TLC to contain the desired product are combined and concentrated to yield the formula-VIII title compound.

Following the procedures of Example 7, steps C, D, E, and F, the beta hydroxy product of step B is transformed to the corresponding 15-epimer of the title compound, viz. 11-deoxy-20-methyl-2-nor-15-epi-PGF$_{2\alpha}$.

Example 8

11-Deoxy-20-methyl-2-nor-PGE$_2$ (Formula VII: A is —(CH$_2$)$_2$—, E is —(CH$_2$)$_4$—, and R$_1$ is hydrogen).

Refer to Chart D. A. There is first prepared 11-deoxy-20-methyl-2-nor-PGE$_2$, 15-tetrahydropyranyl ether (formula XXXV wherein A is —(CH$_2$)$_2$—, L is —(Ch$_2$)$_4$—, and M''' is

wherein THP is tetrahydropyranyl). To a solution of the formula-XXXIII tetrahydropyranyl ether of 11-deoxy-20-methyl-2-nor-PGF$_{2\alpha}$(Example 7, 0.8 g.) in 13 ml. of acetone at −20° C. is added dropwise to 0.88 ml. of Jones reagent (2.1 g. of chromic anhydride, 6 ml. of water, and 1.7 ml. of concentrated sulfuric acid). After 15 min. stirring, 1 ml. of 2-propanol is added, with additional stirring followed by 35 ml. of water. The solution is shaken with three portions of dichloromethane, the organic extracts are combined, dried, and concentrated under reduced pressure. The residue is chromatographed over silica gel to yield a fraction shown by TLC to contain the formula-XXXV compound.

B. The title compound is obtained by hydrolyzing the formula-XXXV tetrahydropyranyl ether (Part A above, 0.7 g.) in a mixture of 5 ml. of THF and 18 ml. of 67% (aqueous) acetic acid maintained at 40° C. for 2–4 hrs. The solvent is removed under reduced pressure, and the residue is chromatographed over silica gel using chloroform-methanol (10:1) for elution. The fractions containing the desired product as shown by TLC are combined and concentrated to yield the formula-VII title compound.

Following the procedures of Example 8, but employing the 15-tetrahydropyranyl ether of 11-deoxy-20-methyl-2-nor-15-epi-PGF$_{2\alpha}$ (following Example 7), there is obtained the 15-epimer of the title compound, viz. 11-deoxy-20-methyl-2-nor-15-epi-PGE$_2$.

Example 9

11-Deoxy-2a-homo-PGF$_{3\alpha}$ (Formula-XI: A is —(CH$_2$)$_4$—, d is 1, and R$_1$ is hydrogen).

Refer to Chart C. A. There is first prepared the 5α-hydroxy-2β-(3α-hydroxy-trans-1-cis-5-octdienyl)-1α-cyclopentaneacetic acid γ-lactone (formula-XXX, wherein L is cis—CH=CH—CH$_2$CH$_3$, and M is

A solution of the hydroxy (S)—(+) phosphonium salt

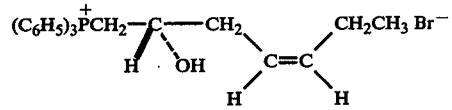

(E. J. Corey et al., J. Am. Chem. Soc. 93, 1490 (1971)) (6.6 g.) in 20 ml. of THF is stired under nitrogen with 2 equivalents of methyllithium first at about −70° C., then at −25° C. for about 30 min. The mixture is cooled to −78° C. and to it is added a solution of the formula-XXVIII 3,3aβ,4β,5,6,6aβ-hexahydro-2-oxo-2H-cyclopenta[b]furan-4-carboxaldehyde (isomer of negative rotation of Example 6, 1.5 g.) in 20 ml. of THF. The mixture is stirred at about −78° C. for 5 min., then at 0° C. for 30 min. The product is separated by extraction into benzene, washing the benzene solution with dilute hydrochloric acid and water, drying over sodium sulfate, and concentrating. The residue is chromatographed on silica gel to yield the formula-XXX intermediate.

B. Following the procedures of Parts C through F of Example 7, replacing the alpha hydroxy intermediate of Part B of that Example with the intermediate of Part A above, and, in Part E, replacing 3-carboxypropyltriphenylphosphonium bromide with 5-carboxypentyltriphenylphosphonium bromide (Preparation 3), there is obtained the 15-tetrahydropyranyl ether of the title compound and, subsequently, the title compound.

Example 10

11-Deoxy-2a-bromo-PGE$_3$ (Formula-X: A is —(CH$_2$)$_4$—, d is 1, and R$_1$ is hydrogen).

Refer to Chart D. Following the procedures of Example 8, but replacing the tetrahydropyranyl ether of that example with the tetrahydropyranyl ether of 11-deoxy-2a-homo-PGF$_{3\alpha}$ (Example 9), there is obtained the tetrahydropyranyl ether of the title compound and subsequently the title compound.

In like manner, following the procedures of Examples 1–4, but employing the appropriate racemic reactants obtained by methods known in the art, there are obtained the corresponding racemic products which are separated and isolated by means known in the art or described herein. There are thereby obtained dl-11-deoxy-15-epi-PGF$_2$, 15-acetate, methyl ester
dl-11-deoxy-15-epi-PGE$_2$, acetate, methyl ester
dl-11-deoxy-15-epi-PGE$_2$
dl-11-deoxy-15-epi-PGE$_2$, methyl ester
dl-11-deoxy-PGE$_2$, methyl ester
dl-11-deoxy-PGF$_{2\alpha}$, 15-acetate, methyl ester
dl-11-deoxy-PGF$_{2\beta}$, 15-acetate, methyl ester
dl-11-deoxy-PGE$_2$, acetate, methyl ester
dl-11-deoxy-PGE$_2$
dl-11-deoxy-PGF$_{2\alpha}$ and
dl-11-deoxy-PGF$_{2\beta}$.

Likewise, following the procedures of Examples 7–10, but employing the appropriate racemic reactants, there are obtained the corresponding racemic products.

There are thereby obtained dl-11-deoxy-20-methyl-2-nor-PGF$_{2\alpha}$ dl-11-deoxy-20-methyl-2-nor-15-epi-PGF$_{2\alpha}$ dl-11-deoxy-20-methyl-2-nor-PGE$_2$ dl-11-deoxy-20-methyl-2-nor-15-epi-PGE$_2$ dl-11-deoxy-2a-homo-PGF$_{3\alpha}$ and dl-11-deoxy-2a-homo-PGE$_3$.

We claim:

1. An optically active compound of the formula

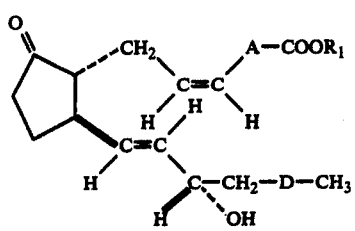

or a racemic compound of that formula and the mirror image thereof, wherein A is alkylene of one to 10 carbon atoms, inclusive, with one to five carbon atoms, inclusive, between —COOR$_1$ and

wherein D is either a valence bond or alkylene of one to nine carbon atoms, inclusive, with one to five carbon atoms, inclusive, in the chain between —CH$_2$— and terminal methyl; inclusive; and wherein R$_1$ is hydrogen, alkyl of one to 12 carbon atoms, inclusive, cycloalkyl of three to 10 carbon atoms, inclusive, aralkyl of seven to 12 carbon atoms, inclusive, phenyl, or phenyl substituted with one, two, or three chloro or alkyl of one to four carbon atoms, inclusive; including the pharmacologically acceptable salts thereof when R$_1$ is hydrogen.

2. A prostanoic acid compound of the formula

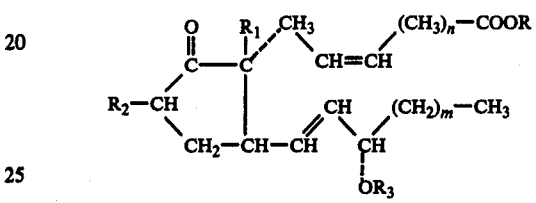

wherein R is selected from the group consisting of hydrogen and alkyl or one to seven carbon atoms, m is 3, 4 or 5, n is 2, 3, or 4, and R$_1$, R$_2$ and R$_3$ are hydrogen and salts thereof with non-toxic, pharmaceutically acceptable bases when R is hydrogen.

3. A compound of claim 3 which is methyl 15$_\alpha$-hydroxy-9-oxo-5-cis 13-trans prostadienoate.

* * * * *

UNITED STATES PATENT AND TRADEMARK OFFICE
CERTIFICATE OF CORRECTION

PATENT NO. : 4,130,721

DATED : 19 December 1978

INVENTOR(S) : G.L. Bundy, et al.

It is certified that error appears in the above—identified patent and that said Letters Patent is hereby corrected as shown below:

Column 10, line 22, "-CH$_2$-CH(CH$_3$)-CH$_2$-, -CH$_2$-, CH$_2$-CH$_2$-CH(CH$_2$CH$_2$CH$_3$)-, and" should read -- -CH$_2$-CH(CH$_3$)-CH$_2$-, -CH$_2$CH$_2$-CH(CH$_2$CH$_2$CH$_3$)-, and --.

Column 10, line 41, "between =C$\langle^H$ " should read -- between -COOR$_1$ and =C$\langle^H$ ; --.

Column 12, line 59, "differnt" should read -- different --.
Column 13, line 22, "-(CH$_2$-" should read -- -CH$_2$- --.
Column 14, line 64, "A. Gutzmán" should read -- A. Guzmán --.
Column 15, line 16, -13,141α," should read -- -13,14-dihydro-PGF$_1$α, --.
Column 22, line 8, "analogy" should read -- analog --.
Column 23, line 60, "condensed purpose," should read -- condensed with --.
Column 27, line 33, "th" should read -- the --.
Column 28, line 56, "lowe alknaol" should read -- lower alkanol --.
Column 29, line 28, "amine ro" should read -- amine to --.
Column 30, line 23, "annd" should read -- and --.
Column 30, line 38, "ethwnol-" should read -- ethanol- --.
Column 32, line 52, "annd R$_1$" should read -- and R$_1$ --.
Column 35, line 29, "-(Ch$_2$)$_4$-" should read -- -(CH$_2$)$_4$- --.

UNITED STATES PATENT AND TRADEMARK OFFICE
CERTIFICATE OF CORRECTION

PATENT NO. : 4,130,721
DATED : 19 December 1978
INVENTOR(S) : G.L. Bundy, et al.

It is certified that error appears in the above—identified patent and that said Letters Patent is hereby corrected as shown below:

Column 36, line 16, "is stired" should read -- is stirred --.
Column 36, line 20, "3,3aβ,4β,5,6,6aβ-" should read -- 3,3aβ,4α,5,6,6aβ- --.
Column 38, line 32, "claim 3" should read -- claim 2 --.

Signed and Sealed this

Tenth Day of November 1981

[SEAL]

Attest:

GERALD J. MOSSINGHOFF

Attesting Officer     Commissioner of Patents and Trademarks